(12) United States Patent
Lee

(10) Patent No.: US 11,123,531 B2
(45) Date of Patent: Sep. 21, 2021

(54) INTEGRATED-TYPE MICRONEEDLE PATCH

(71) Applicant: Sanghyuk Lee, Anyang-si (KR)

(72) Inventor: Sanghyuk Lee, Anyang-si (KR)

( * ) Notice: Subject to any disclaimer, the term of this patent is extended or adjusted under 35 U.S.C. 154(b) by 224 days.

(21) Appl. No.: 16/474,262

(22) PCT Filed: May 10, 2019

(86) PCT No.: PCT/KR2019/005619
§ 371 (c)(1),
(2) Date: Jun. 27, 2019

(87) PCT Pub. No.: WO2020/130240
PCT Pub. Date: Jun. 25, 2020

(65) Prior Publication Data
US 2020/0338327 A1 Oct. 29, 2020

(30) Foreign Application Priority Data
Dec. 20, 2018 (KR) .................. 10-2018-0166488

(51) Int. Cl.
*A61M 37/00* (2006.01)
(52) U.S. Cl.
CPC . *A61M 37/0015* (2013.01); *A61M 2037/0023* (2013.01); *A61M 2037/0046* (2013.01); *A61M 2037/0061* (2013.01)
(58) Field of Classification Search
CPC ...... A61M 37/0015; A61M 2037/0023; A61M 2037/0046; A61M 2037/0061; A61K 8/735; A61K 2800/10; A61K 8/0208; A61K 9/0021; A61K 9/703; A61Q 19/00
See application file for complete search history.

(56) References Cited

U.S. PATENT DOCUMENTS

2008/0214952 A1* 9/2008 Mir .................. A61M 37/0015
600/556

FOREIGN PATENT DOCUMENTS

KR    10-1618523 B1    5/2016
KR    10-1746024 B1    6/2017

OTHER PUBLICATIONS

Merriam-Webster Dictionary definition for "leak". Accessed Jul. 6, 2021 at merriam-webster.com/dictionary/leaking. (Year: 2021).*

* cited by examiner

*Primary Examiner* — Amber R Stiles
(74) *Attorney, Agent, or Firm* — Rabin & Berdo, P.C.

(57) ABSTRACT

An integrated-type microneedle patch according to the present invention includes: a needle unit (10) including an array of microneedles (12) for skin puncturing, and a needle base (11) supporting the array of the microneedles (12); an active ingredient portion (30) containing an active ingredient that consists of a drug or a functional cosmetic ingredient; and a patch unit (20) including a protective patch layer (21) covering the active ingredient portion (30) and protecting skin after a procedure, wherein the active ingredient portion (30) is located toward the skin with respect to the protective patch layer (21), and the needle base (11) is located opposite to the skin with respect to the protective patch layer (21), whereby the needle unit (10) is separated from the patch unit (20) after a skin puncture procedure using the microneedles (12) is performed.

2 Claims, 5 Drawing Sheets

INTEGRATED-TYPE MICRONEEDLE PATCH

TECHNICAL FIELD

The present invention relates generally to a microneedle patch provided in an integrated type and, more particularly, to a microneedle patch for medical use or cosmetic use.

BACKGROUND ART

A microneedle or microneedle patch is a well known technique for increasing permeation of an active ingredient into the skin through micro-holes created by microneedles, thus increasing the rate of absorption into the skin.

FIG. 1 is a perspective view showing a main configuration of a typical microneedle patch.

Multiple microneedles 1 provided in the form of micron-scale needles are fixed by a base substrate 2. The base substrate 2 is fixed to an attachment portion 3 and is attached to the skin by the attachment portion 3. The microneedles 1 create channels through which an active ingredient is delivered into the skin.

Recent developments in microneedle patch technology have been focused on a dissolvable microneedle (hereinafter also referred to as "needle") which itself contains an active ingredient.

According to the technique of Patent Document 1, there is disclosed a microneedle in which porous particles are provided on the surface or at least in a part of the inside of a biocompatible matrix in the form of a microneedle, such that a filler optimized for efficiency due to an increased surface area of the porous particles is supplied.

Furthermore, according to the technique of Patent Document 2, there is disclosed a microneedle coated with a porous coating layer, the microneedle capable of securing a flow path through which a drug is delivered and formed in the surface of a needle body, and improving efficiency in drug absorption and drug delivery by utilizing the advantages of a material.

To this end, the microneedle coated with the porous coating layer includes a needle body having rigidity to penetrate the epidermal layer and a coating layer coated to cover the needle body. The needle body is made of a highly rigid material containing metal or silicon. The coating layer has multiple communication holes depressed or formed therethrough so as to be filled with a drug, and the communication holes communicate with each other to form a flow path of the drug.

As in Patent Document 2, in the case where the needle body is made of a highly rigid material in addition to the active ingredient contained in the needle to increase the rigidity of the needle, the needle body may remain in the skin without dissolution after a microneedle patch is attached. This may cause a user discomfort, such as a feeling of slight stinging in the skin, which occurs due to movement of a user.

In order to improve user comfort by reducing such a feeling of stinging, it is preferable that the needle is completely dissolved by body temperature or the like as in Patent Document 1.

However, such a dissolvable needle has other problems. First, the needle which itself contains an active ingredient may be technically very demanding to manufacture, and the physical properties of the active ingredient may be limited.

Additionally, when the needle itself is constituted to contain an active ingredient, the rigidity of the needle may be low. This may cause a problem in that the needle, particularly a tip portion thereof, is broken in the process of attaching the needle patch to the skin, and thus permeation of the active ingredient is not very effective. Furthermore, in order to form microneedles containing an active ingredient by a molding method, heating is required, which may cause a problem of adversely affecting the active ingredient.

The foregoing is intended merely to aid in the understanding of the background of the present invention, and is not intended to mean that the present invention falls within the purview of the related art that is already known to those skilled in the art.

(Patent Document 1) Korean Patent No. 10-1618523 (registered on Apr. 28, 2016) "MICRO-NEEDLE AND MICRO-NEEDLE PATCH"

(Patent Document 2) Korean Patent No. 10-1746024 (registered on Jun. 5, 2017) "MICRONEEDLE COATED WITH POROUS COATING LAYER, MANUFACTURING METHOD THEREOF, AND MICRONEEDLE PATCH HAVING MICRONEEDLE"

DISCLOSURE

Technical Problem

Accordingly, the present invention has been made keeping in mind the above problems occurring in the related art, and an objective of the present invention is to provide an integrated-type microneedle patch capable of freely constituting needles with a high rigidity while causing no feeling of stinging after attachment.

Another objective of the present invention is to provide an integrated-type microneedle patch, capable of constituting an active ingredient having various physical properties without any restriction on the physical properties of the active ingredient.

Technical Solution

In order to achieve the above objectives, according to one aspect of the present invention, there is provided an integrated-type microneedle patch, including: a needle unit 10 including an array of microneedles 12 for skin puncturing, and a needle base 11 supporting the array of the microneedles 12; an active ingredient portion 30 containing an active ingredient that consists of a drug or a functional cosmetic ingredient; and a patch unit 20 including a protective patch layer 21 covering the active ingredient portion 30 and protecting skin after a procedure, wherein the active ingredient portion 30 is located toward the skin with respect to the protective patch layer 21, and the needle base 11 is located opposite to the skin with respect to the protective patch layer 21, whereby the needle unit 10 is separated from the patch unit 20 after a skin puncture procedure using the microneedles 12 is performed.

The integrated-type microneedle patch may further include a buffer portion 40 interposed between the needle base 11 and the protective patch layer 21, and having a shape surrounding the array of the microneedles 12 to protect the array of the microneedles 12, the buffer portion being configured to be compressed or collapse when the needle unit 10 is pressed such that a height thereof is lowered.

The integrated-type microneedle patch may further include: a first adhesive portion 51 bonding the needle base 11 and the buffer portion 40; and a second adhesive portion 52 bonding the buffer portion 40 and the protective patch layer 21, wherein an adhesive force exerted by the first adhesive portion 51 may be stronger than an adhesive force exerted by the second adhesive portion 52 such that when the needle unit 10 is separated, the buffer portion 40 is separated together therewith.

In the integrated-type microneedle patch, the patch unit 20 may further include an adhesive layer provided on a surface of the protective patch layer 21 for adhering to the skin at a position on the surface of the protective patch layer 21 that surrounds the active ingredient portion 30.

In the integrated-type microneedle patch, holes that are created in the protective patch layer 21 upon the skin puncture procedure using the microneedles may be sealed after the microneedles are removed.

In the integrated-type microneedle patch, the active ingredient may be in a liquid state, and the active ingredient portion 40 may be configured such that the liquid active ingredient is contained inside a pocket 32 in a hermetically sealed manner.

In the integrated-type microneedle patch, the patch unit 20 may further include a sealing layer 23 provided at a position between a protective patch layer 21 and an active ingredient portion 30, or at a position on a surface of the protective patch layer 21, and allowing holes that are created upon the skin puncture procedure using the microneedles to be sealed after the microneedles are removed, thus preventing external leakage of the active ingredient.

Advantageous Effects

According to the present invention having the above-described characteristics, it is possible to provide a microneedle patch capable of freely constituting needles with a high rigidity while causing no feeling of stinging after attachment.

While, in the related art, there is a problem in that microneedles that are dissolvable and have rigidity remain in the skin after a procedure thus causing a feeling of stinging, in the present invention, it is possible to easily separate a needle unit from a patch unit after a skin puncture procedure using the microneedles is performed, thus completely removing the microneedles having rigidity after the procedure.

Furthermore, in the related art, an active ingredient in a liquid state is difficult to use in a microneedle patch. However, in the present invention, it is possible to easily apply the liquid active ingredient to the microneedle patch.

BEST MODE

Figure 1:
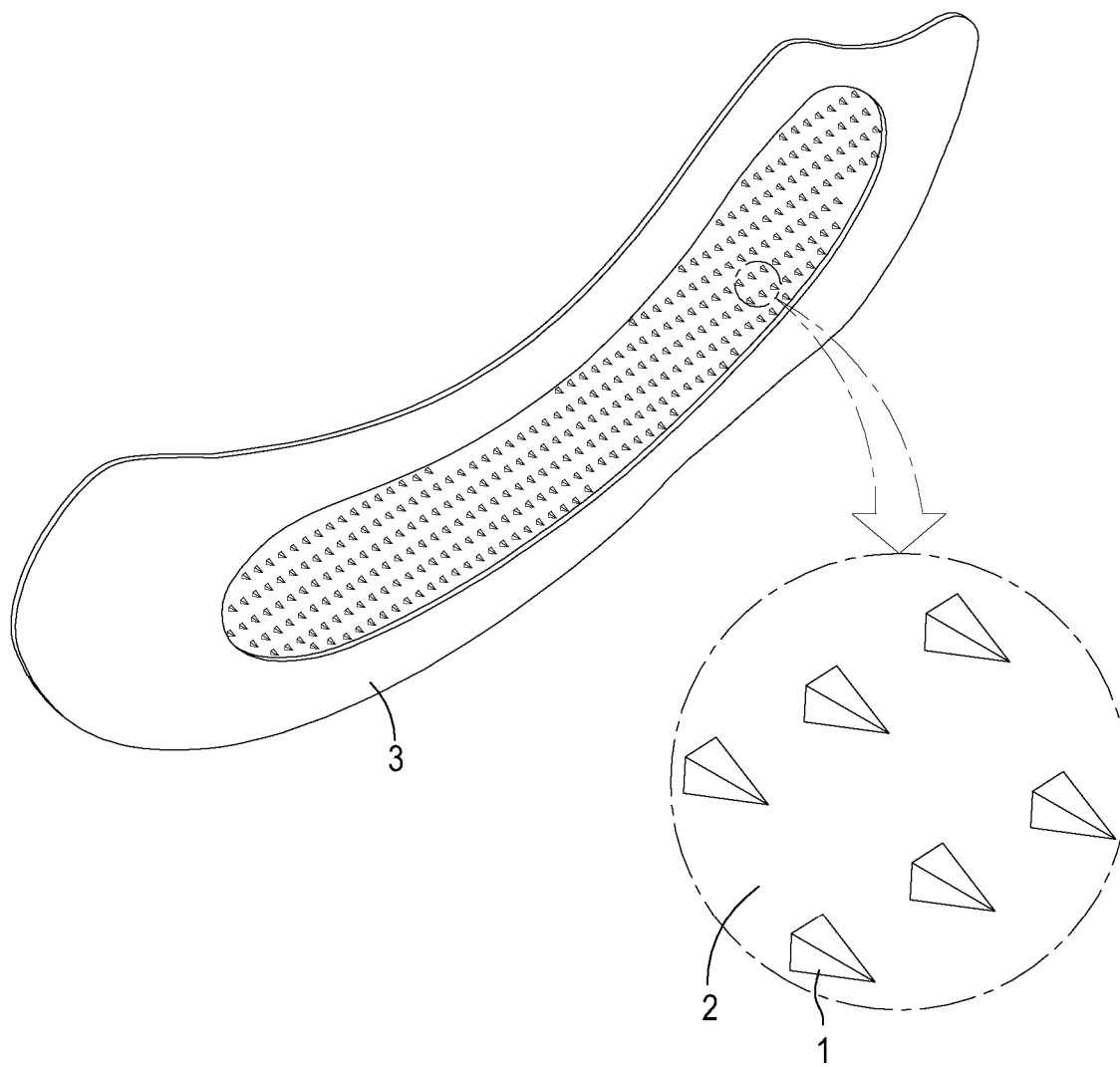
FIG. 1 is a perspective view showing a main configuration of a typical microneedle patch.

Hereinbelow, exemplary embodiments of the present invention will be described in detail with reference to the accompanying drawings such that the invention can be easily embodied by one of ordinary skill in the art to which this invention belongs. However, it should be understood that the embodiments may be changed to a variety of embodiments and the scope and spirit of the invention are not limited to the embodiments described hereinbelow. In the following description, it is to be noted that, when the functions of conventional elements and the detailed description of elements related with the present invention may make the gist of the present invention unclear, a detailed description of those elements will be omitted. Throughout the drawings, the same reference numerals will refer to the same or like parts.

Figure 2:
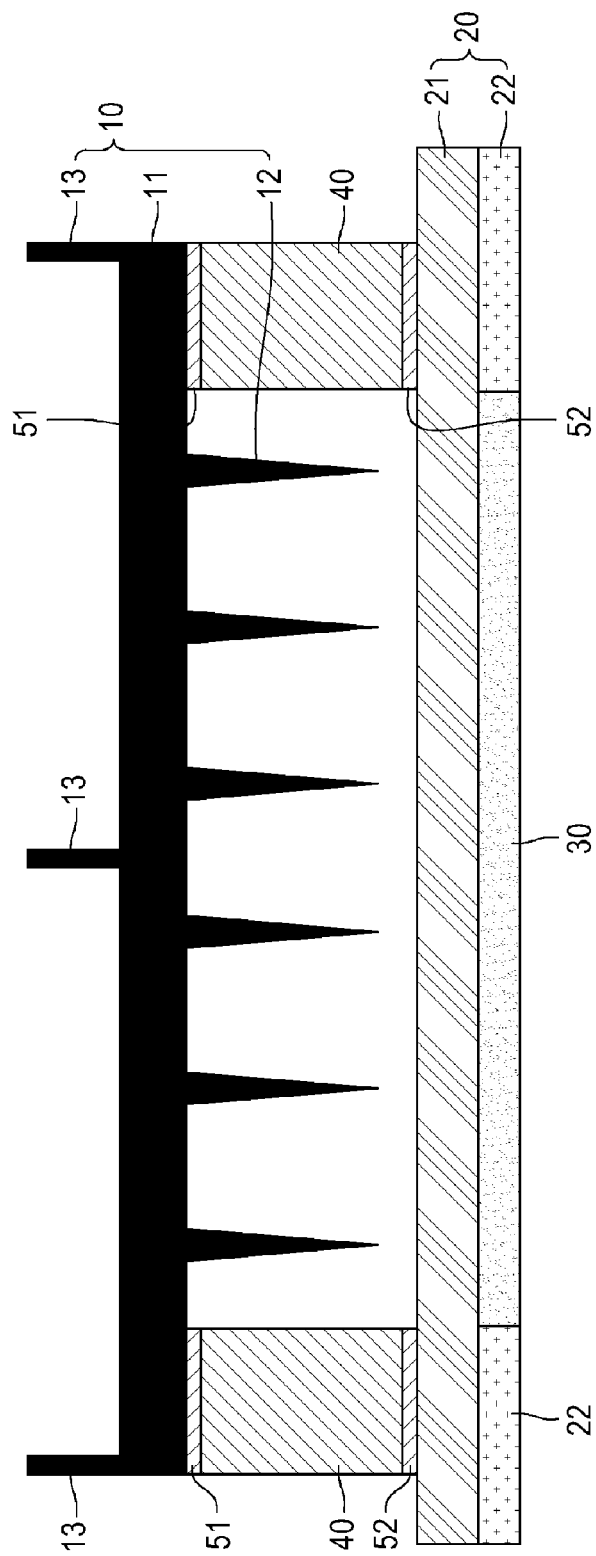
FIG. 2 is a sectional view showing a structure of a microneedle patch according to a first embodiment of the present invention.

FIG. 2 is a sectional view showing a structure of a microneedle patch according to a first embodiment of the present invention.

In FIG. 2, the upper and lower sizes (height) are exaggerated in comparison with the left and right sizes for convenience of explanation.

Microneedle patches may have various sizes and shapes when viewed from above (in a plan view) and may be shaped to conform to the size, curvature, and shape of application regions, such as under the eyes, around the mouth, arms, hands, shoulders, and abdomen. For example, in the case of a microneedle patch attached under the eyes, the shape thereof may be the shape shown in FIG. 1.

The microneedle patch according to the first embodiment of the present invention includes a needle unit 10, a patch unit 20, an active ingredient portion 30, a buffer portion 40, and first and second adhesive portions 51 and 52.

The needle unit 10 includes an array of microneedles 12 for skin puncturing and a planar plate-shaped needle base 11 for fixing and supporting the array of the microneedles 12. The microneedles 12 may have a sharp cone or a sharp polygonal cone shape.

The microneedles 12 arranged in an array are made of metal or plastic having a height of about 0.25 mm. The microneedles 12 and the needle base 11 may be integrally formed by injection molding with a plastic material. Alternatively, the microneedles 12 made of metal may be fixed by the needle base 11 made of plastic.

The needle unit 10 may be removed after a skin puncture procedure by pulling the needle unit 10 so as to be separated from the patch unit 20. A base protrusion 13 protrudes from the needle base 11 and may be used as a handle when separating the needle unit from the patch unit 20 by pulling the needle unit 10. In addition, bridges or the like that extend from opposite base protrusions 13 and are connected to each other may be provided such that a structure used in separation and removal of the needle unit is further provided.

Although tip portions of the microneedles 12 are shown as being provided outside a protective patch layer 21 in the drawings, the tip portions of the microneedles 12 may be provided in the protective patch layer 21, in the active ingredient portion 30, or below the active ingredient portion 30. At this time, this may be easily achieved by a way of differently designing the height of the buffer portion 40.

The patch unit 20 includes the protective patch layer 21 and an adhesive layer 22 and is fixed to the skin after a skin puncture procedure by covering a puncture site of the skin in a state of covering the active ingredient portion 30. The patch unit prevents external leakage of an active ingredient and protects from infection or the like the skin layer in which puncture holes, so-called micro-injuries, are created.

The protective patch layer 21 covers the active ingredient portion 30 containing an active ingredient and protects the skin after a procedure. The protective patch layer may be made of various materials such as hydrocolloids that can be used in general patches or band aids and may be made of a material that can be easily bendable conforming to the curvature of the skin surface.

The adhesive layer 22 is provided on the surface of the protective patch layer 21 for adhering to the skin at a position surrounding the active ingredient portion 30 when viewed in a plan view. The adhesive layer 22 is fixed to the skin due to an adhesive force thereof after a procedure and prevents the active ingredient from leaking to the side when viewed in a plan view.

The protective patch layer 21 may have holes that are created by the microneedles 12 when the microneedles 12 puncture the skin during a skin puncture procedure. Such holes created in the protective patch layer 21 may not be completely sealed after the removal of the microneedles 12 but are preferably sealed.

The active ingredient portion 20 may contain only the active ingredient consisting of a drug or functional cosmetic substances, or may contain another substance or structure in addition to the active ingredient. The active ingredient is biodegradable or soluble in biological tissue at the time of skin puncturing and typically uses hyaluronic acid (HA). An example of the active ingredient may include at least one of chitosan, collagen, gelatin, alginic acid, pectin, carrageenan, chondroitin (sulfate), dextran (sulfate), polylysine, carboxymethyltin, fibrin, agarose, pullulan, and cellulose, or a combination thereof.

In the microneedle patch according to the first embodiment of the present invention, the active ingredient contained in the active ingredient portion is preferably in a solid state and is preferably a type that is dissolved in response to moisture and/or body temperature of the skin when in contact with the skin.

The active ingredient portion 30 is naturally located toward the skin with respect to the protective patch layer 21. Usually, the needle base 11 of the needle unit 10 is located opposite to the skin with respect to the protective patch layer 21. The microneedles 12 of the needle unit 10 are located opposite to the skin with respect to the protective patch layer 21 as shown in the drawings. As occasion demands, the tip portions of the microneedles may penetrate the protective patch layer 21 or the active ingredient portion 30. However, in either case, at least the needle base 11 among the constituent elements of the needle unit 10 is provided opposite to the skin with respect to the protective patch layer 21.

Therefore, the present invention is characterized in that the needle unit 10 can be easily separated from the patch unit 20 after a skin puncture procedure using the microneedles 12 is performed.

According to the related art, all the elements corresponding to the needle base 11 are provided at positions toward the skin with respect to the protective patch layer 21, that is, the protective patch layer 21 inwardly covers the elements corresponding to the needle base 11. Due to this, it is impossible or very inconvenient to remove the needle base.

Therefore, in the related art, there is a problem in that microneedles that are dissolvable and have rigidity remain in the skin after a procedure, thus causing a feeling of stinging. However, according to the present invention, the microneedles having rigidity can be completely removed after a procedure.

The buffer portion 40 is interposed between the needle base 11 and the protective patch layer 21. The buffer portion has a shape surrounding the array of the microneedles 12 when viewed in a plan view, thus forming a fence shape that protects the array of the microneedles 12. When the needle unit 10 is pressed, the buffer portion is compressed or collapses and the height thereof is lowered, such that the microneedles 12 create puncture holes of a sufficient depth in the skin.

The buffer portion 40 may be made of a material such as Styrofoam, rubber, paper, or the like. The buffer portion is shown simply as having a quadrangular cross-sectional structure in the drawings, but may have various cross-sectional structures such as a bellows shape, a porous structure, a honeycomb shape, a staple shape, and the like.

Due to the characteristics the material itself or the structure described above, the buffer portion 40 has elasticity in at least an upward-and-downward direction and is deformable in response to an external force.

At the time of product shipping and product storage, the buffer portion 40 supports the needle unit 10 and allows the needle unit 10 to be coupled to and held by the patch unit 20. At the time of a skin puncture procedure, the buffer portion is compressed or collapses while being pressed by the needle base 11 so as to allow the tip portions of the microneedles 12 to sequentially penetrate the protective patch layer 21, the active ingredient portion 30, and the skin.

The first and second adhesive portions 51 and 52 are respectively provided on opposite surfaces of the buffer portion 40 for bonding with the needle unit 10 and the patch unit 20. The first adhesive portion 51 is provided on a first surface of the buffer portion 40 to bond the needle base 11 and the buffer portion 40. The second adhesive portion 52 is provided on a second surface of the buffer portion 40 to bond the buffer portion 40 and the protective patch layer 21.

Furthermore, the adhesive force exerted by the first adhesive portion 51 may be stronger than the adhesive force exerted by the second adhesive portion 52 such that when the needle unit 20 is separated, the buffer portion 40 is separated together therewith.

In the microneedle patch, there may be further provided a cover sheet (not shown) covering the exposed surfaces of the active ingredient portion 30 and/or the adhesive layer 22. Furthermore, the microneedle patch may be manufactured and distributed in a state of being stored in a casing (not shown).

Figure 3:
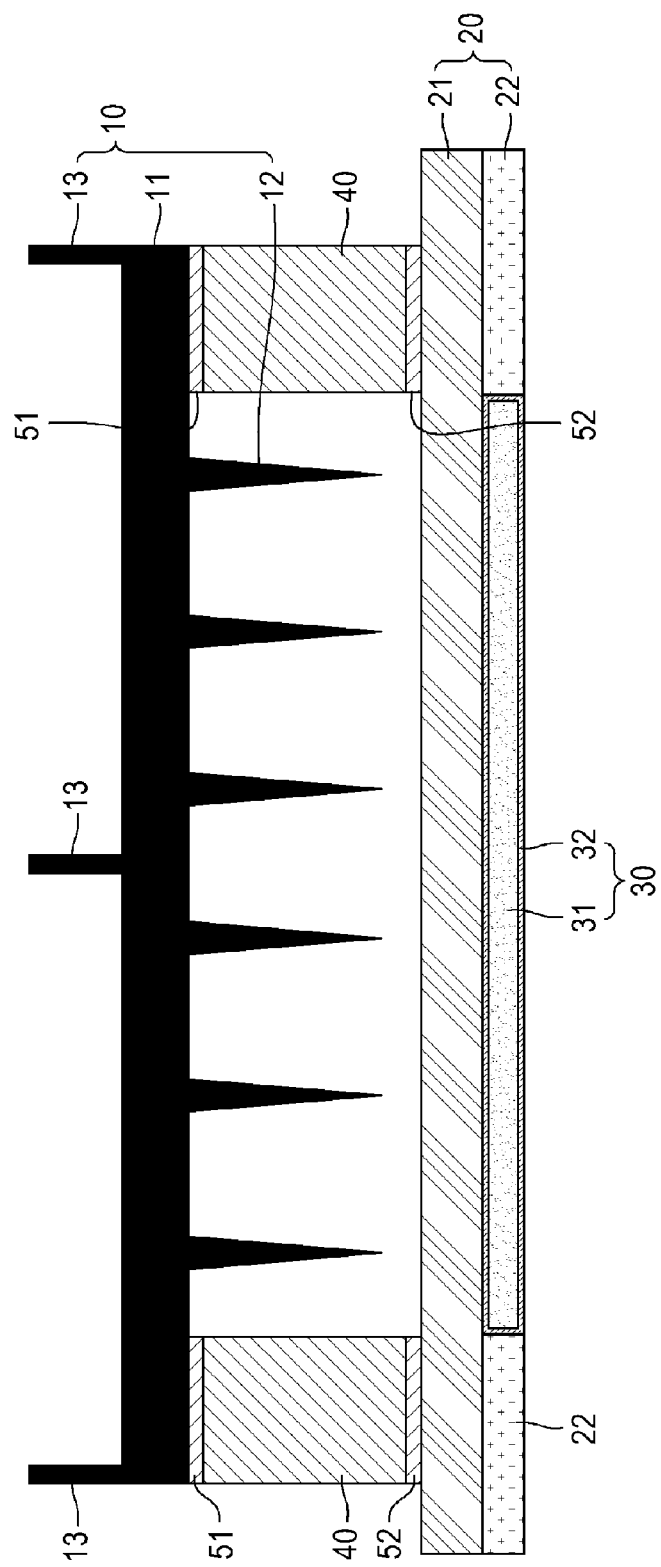
FIG. 3 is a sectional view showing a structure of a microneedle patch according to a second embodiment of the present invention.

FIG. 3 is a sectional view showing a structure of a microneedle patch according to a second embodiment of the present invention.

The structure of the second embodiment is very similar to the structure of the first embodiment, and thus a description of similar parts will be omitted and a description will be mainly given to different parts.

In the second embodiment, an active ingredient 31 is in a liquid state. An active ingredient portion 40 is configured such that the liquid active ingredient 31 is contained inside a pocket 32 in a hermetically sealed manner. The pocket 32 may have a planar plate-shaped pocket made of a resin such as vinyl or the like. The pocket 32 may store the liquid active ingredient in a hermetically sealed manner by a method of injecting the liquid active ingredient into the pocket and then sealing or bonding an injection opening.

While most medicinal substances or cosmetic substances are often in a liquid state, according to the related art, an active ingredient in a liquid state is difficult to use in a microneedle patch. However, in the case of the microneedle patch according to the second embodiment of the present invention constructed as described above, it is possible to easily apply the liquid active ingredient to the microneedle patch.

Figure 4:
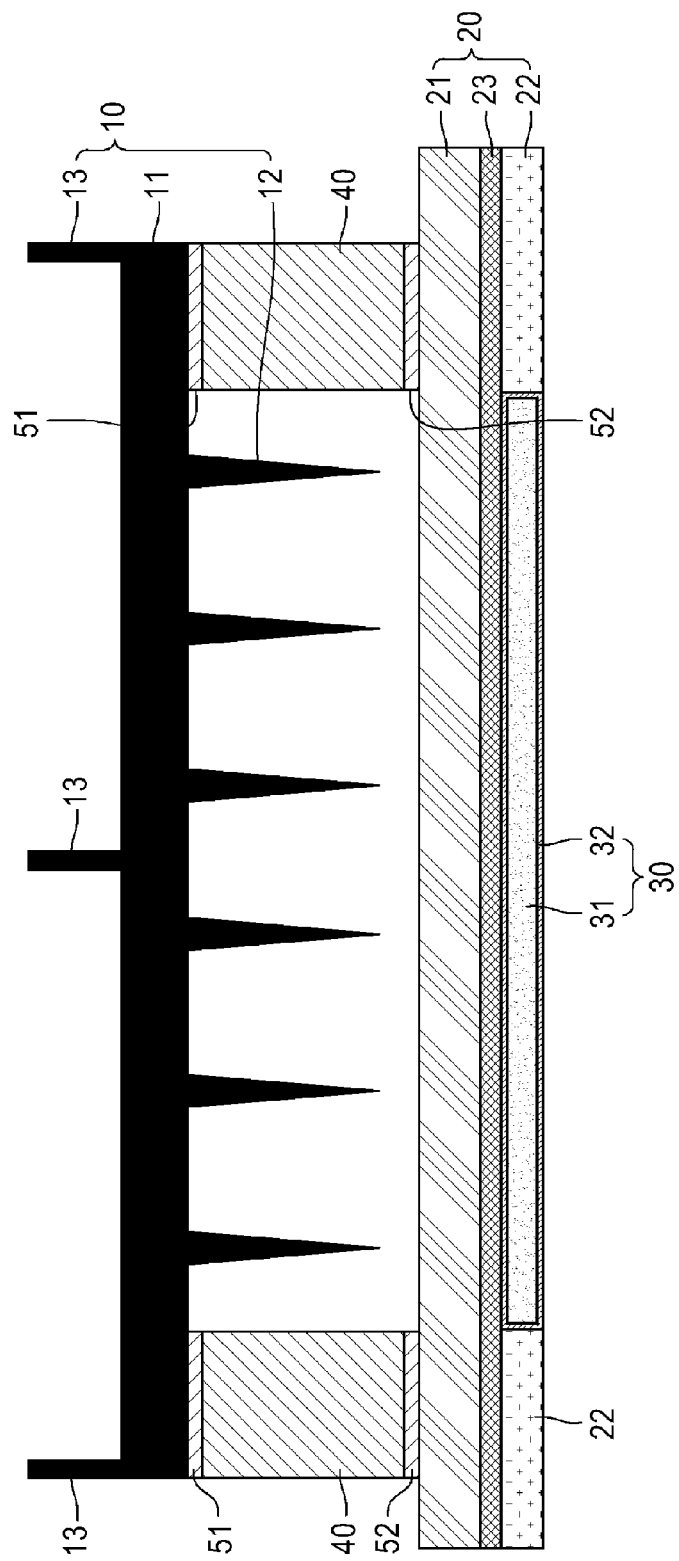
FIG. 4 is a sectional view showing a structure of a microneedle patch according to a modification of the present invention.

FIG. 4 is a sectional view showing a structure of a microneedle patch according to a modification of the present invention.

The structure of the modification is very similar to the structure of the second embodiment or the first embodiment, and thus a description of similar parts will be omitted and a description will be mainly given to different parts.

In the modification, a patch unit 20 further includes a sealing layer 23. The sealing layer 23 is provided at a position between a protective patch layer 21 and an active ingredient portion 30 (see FIG. 4), or at a position on the surface of the protective patch layer 21 opposite to the skin. The sealing layer is made of a material that allows holes created upon a skin puncture procedure using microneedles to be completely sealed after removal of the microneedles, thus preventing external leakage of an active ingredient, particularly an active ingredient in a liquid state.

The sealing layer 23 may be made of various materials based on rubber. In this case, it is particularly useful when the protective patch layer 21 can not prevent or lacks an ability to prevent external leakage of the active ingredient.

Figure 5:
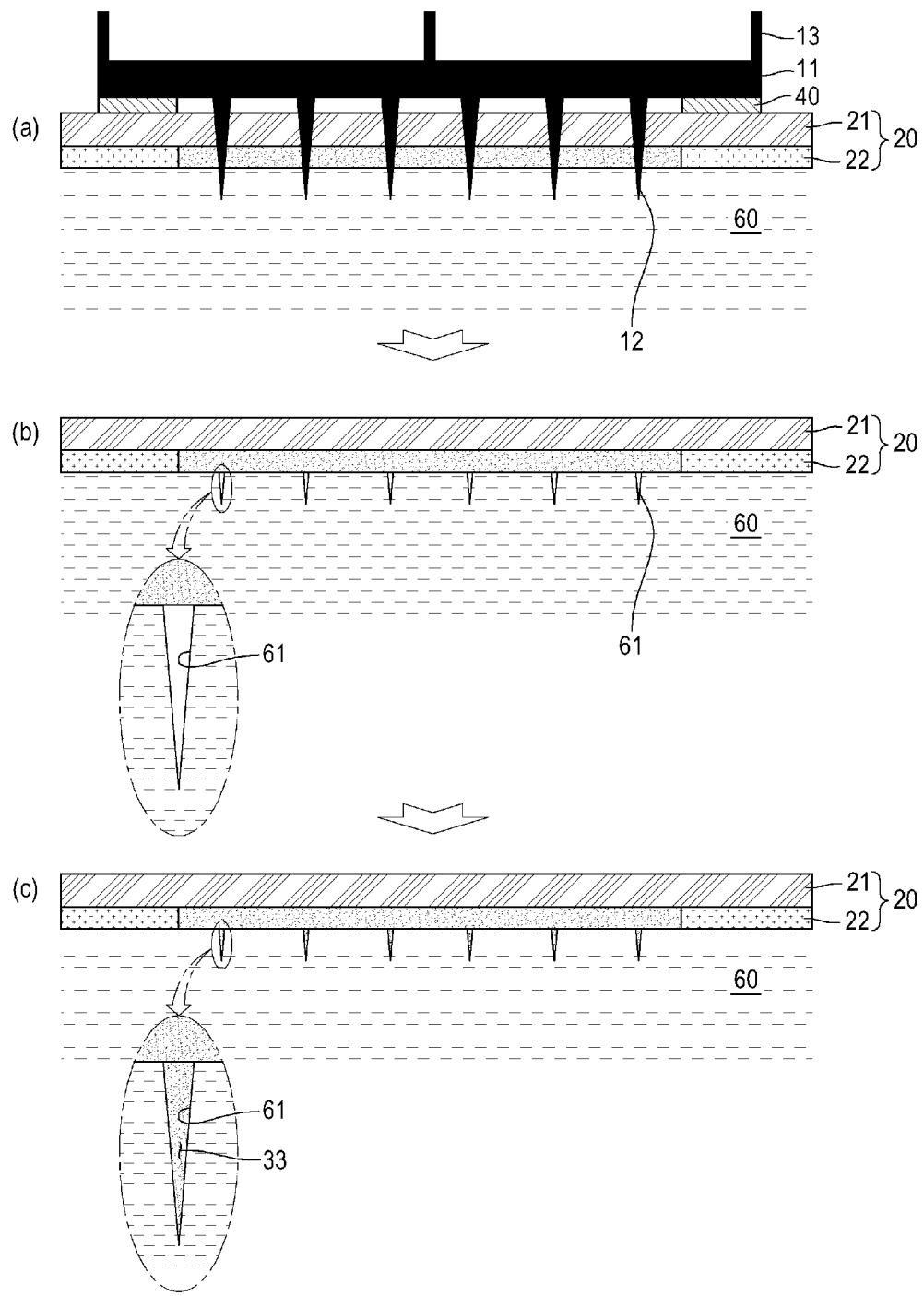
FIG. 5 illustrates views showing a procedure using the microneedle patch according to the present invention.

FIG. 5 illustrates views showing a procedure using the microneedle patch according to the present invention.

In FIG. 5, although the microneedle patch according to the first embodiment of the present invention is shown as a reference, the microneedle patches of the other embodiments are also similar.

As shown in FIG. 5a, a practitioner or a user presses the needle unit 10 while putting the lower surface of the microneedle patch on a skin site to be treated, causing the tip portions of the microneedle 12 to sequentially penetrate the protective patch layer 21 and the active ingredient portion 30 and causing puncture holes 61 to be created in a skin 60. At this time, the buffer portion 40 of the micro-needle patch is compressed or collapses and the height thereof is lowered. In this process, the protective patch layer 21 adheres to the skin 60 to some extent by the adhesive layer 22 of the micro-needle patch.

After the puncture holes 61 having a desired depth are created in the skin 60, the practitioner or the user can separate and remove the needle unit 10 from the patch unit 20, for example, by pulling the needle unit 10, that is, the base protrusions 13 of the needle unit 10 with one hand while pressing the edge of the protective patch layer 21 with the other hand. FIG. 5b shows a state the needle unit 10 is removed in the above-described manner. Then, the patch unit 20 may be pressed such that skin adhesion by the adhesive layer 22 can be more surely performed.

As shown in FIG. 5c, the active ingredient in a solid state is dissolved by the body temperature and/or moisture of the skin over time. A dissolved active ingredient 33 is diffused through the puncture holes 61 into the skin, that is, into the dermal layer.

Furthermore, in the case where the active ingredient portion 30 has a pocket shape containing a liquid active ingredient as in the second embodiment (see FIG. 3) or in the modification (see FIG. 4), holes are created in opposite surface of the pocket by the tip portions of the microneedles 12 at respective positions where the microneedles 12 are arranged.

At this time, the liquid active ingredient flowing out through the holes located opposite to the skin is blocked by the sealed protective patch layer 21 or the sealed sealing layer 23, while the liquid active ingredient flowing out through the holes located toward the skin rapidly fills the puncture holes 61, thus deeply permeating into the skin at a faster rate.

What is claimed is:

1. An integrated-type microneedle patch, comprising:
a needle unit including an array of microneedles for skin puncturing, and a needle base supporting the array of the microneedles;
an active ingredient portion containing an active ingredient that consists of a drug or a functional cosmetic ingredient; and
a patch unit including a protective patch layer covering the active ingredient portion and protecting skin after a skin puncture procedure,
wherein the active ingredient portion is located toward the skin with respect to the protective patch layer, and the needle base is located opposite to the skin with respect to the protective patch layer, whereby the needle unit is separated from the patch unit after the skin puncture procedure using the microneedles is performed,
wherein the microneedle patch further comprises:
a buffer portion interposed between the needle base and the protective patch layer, and having a shape surrounding the array of the microneedles to protect the array of the microneedles, the buffer portion being configured to be compressed or collapse when the needle unit is pressed such that a height thereof is lowered;
a first adhesive portion bonding the needle base and the buffer portion; and
a second adhesive portion bonding the buffer portion and the protective patch layer,
wherein an adhesive force exerted by the first adhesive portion is stronger than an adhesive force exerted by the second adhesive portion such that when the needle unit is separated, the buffer portion is separated together therewith.

2. The integrated-type microneedle patch of claim 1, wherein the patch unit further includes:
an adhesive layer provided on a surface of the protective patch layer for adhering to the skin at a position on the surface of the protective patch layer that surrounds the active ingredient portion.

* * * * *